(12) United States Patent
Wellstein et al.

(10) Patent No.: US 7,141,384 B1
(45) Date of Patent: Nov. 28, 2006

(54) DETECTION OF PLEIOTROPHIN

(75) Inventors: Anton Wellstein, Washington, DC (US); Boussad Souttou, Paris (FR); Daniel Raulais, Paris (FR); Marc Vigny, Paris (FR)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/806,820

(22) PCT Filed: Oct. 6, 1999

(86) PCT No.: PCT/US99/23220

§ 371 (c)(1),
(2), (4) Date: Feb. 12, 2002

(87) PCT Pub. No.: WO00/20869

PCT Pub. Date: Apr. 13, 2000

Related U.S. Application Data (60) Provisional application No. 60/103,197, filed on Oct. 6, 1998.

(51) Int. Cl.
*G01N 33/567* (2006.01)
(52) U.S. Cl. .................. 435/7.21; 435/7.1; 435/7.2; 435/7.23
(58) Field of Classification Search ............... 435/7.1, 435/7.2, 7.21, 7.23, 7.9, 7.91, 7.92, 7.94, 435/810
See application file for complete search history.

(56) References Cited

U.S. PATENT DOCUMENTS 4,281,061 A * 7/1981 Zuk et al.

FOREIGN PATENT DOCUMENTS

| WO | WO 96/02257 A | 2/1996 |
|---|---|---|
| WO | WO 99/07407 A | 2/1999 |

OTHER PUBLICATIONS

Choudhuri et al Cancer Research vol. 57 p. 1814 (1997).*
Yolken, Reviews of Infectious Disease vol. 4 p. 35 (1982).*
Milstein et al Nature vol. 256 p. 495 (1975).*
Ichikawa et al., A highly sensitive enzyme immunoassay for G-CSF in human plasma, Exp Hematol., Mar. 1995; 23 (3) :192-5, abstract only.
Helle et al., "Sensitive ELISA for interleukin-6. Detection of IL-6 in biological fluids; synovial fluids and sera", J Immunol Methods., Apr. 8, 1991; 138 (1): 47-56, abstract only.
Morita et al., "Development of a sensitive enzyme-linked immunosorbent assay for eotaxin and measurement of its levels in human blood", J Immunol Methods., Jun. 24, 1999; 226 (1-2): 159-67, abstract only.
van der Pouw Kraan et al., "Characterisation of monoclonal antibodies to human IL-4: application in an IL-4 ELISA and differential inhibition of IL-4 bioactivity on B cells and T cells", Eur Cytokine Netw., Sep.-Oct. 1993; 4 (5): 343-9, abstract only.
Ida et al., "A highly sensitive enzyme-linked immunosorbent assay for the mesaurement of interleukin-8 in biological fluids", J Immunol Methods., Nov. 25, 1992; 156 (1): 27-38, abstract only.
De Groote et al., "Characterisation of monoclonal antibodies against human interleukin-10 and their use in an ELISA for the measurement of this cytokine", J Immunol Methods., Dec. 28, 1994; 177 (1-2): 225-34, abstract only.
Kiss et al., "Determination of IL6, IL1, and IL4 in the plasma of patients with multiple myeloma", Leuk Lymphoma., Jul 1194; 14 (3-4): 335-40, abstract only.
Fukuda et al., "A sandwich enzyme-linked immunosorbent assay for human interleukin-5", J Immunol Methods., Sep. 20, 1992; 143 (1): 89-94, abstract only.
Ida et al., "An enyzme-linked immunosorbent assay for the measurement of human interleukin-6", J Immunol Methods., Oct. 19, 1990; 133 (2); 279-84, abstract only.
Adolf, GR, "Monoclonal antibodies and enzyme immunoassays specific for human interferon (IFN) omega 1: evidence that IFN-omega 1 is a component of human leukocyte IFN", Virology, Apr. 1990; 175 (2): 410-7. abstract only.
Ellis et al., "Capture immunoassay for ruminant tumor necrosis factor-alpha: comparison with bioassay," Vet Immunol Immunopathol., Jan. 1993; 35 (3-4): 289-300, abstract only.
Petyovka et al., "Homologous ELISA for detection of oligomeric human TNF: properties of the assay," J. Immunol Methods., Oct. 26, 1995; 186 (2): 161-70, abstract only.
van der Meide et al., "A sensitive two-site enzyme immunoassay for the detection of rat interferon-gamma in biological fluids." J. Interferon Res., Apr. 1990; 10 (2): 183-9, abstract only.
Nan Zhang et al., "Human Breast Cancer Growth Inhibited in Vivo by a Dominant Negative Pleiotrophin Mutant", The Journal of Biological Chemistry, vol. 272 ( No. 27), pp. 16733-16736, (Jul. 4, 1997).
International Search Report for International Patent Application No. PCT/US99/23220, mailed on Feb. 4, 2000.
Supplementary European Search Report for European Patent Application No. 99951799.8, mailed on Dec. 17, 2001.
Beau et al., 1995, "Retinoic acid-induced heparin binding protein (RIHB) binds to embryonal chondrocytes and cartilage primarily via proteoglycans", Exp. Cell Res., 218(2):531-539 (abstract only).
Brigstock et al., 1996, "Pig uterine luminal fluid contains the developmentally regulated neurotophic factor, pleiotrophin", J. Endocrinology, 148(1):103-111 (abstract only).

(Continued)

*Primary Examiner*—Sheela J. Huff
(74) *Attorney, Agent, or Firm*—Pillsbury Winthrop Shaw Pittman LLP (57) ABSTRACT

The invention relates to a novel method and kit for detecting and measuring pleiotrophin in samples and diagnosing pleiotrophin-positive diseases. The method involves incubating a sample suspected of containing PTN with anti-PTN antibodies and determining the presence of PTN using a sandwich ELISA. Also methods for treating a pleiotrophin-positive disease by administering an anti-PTN antibody or fragment thereof are provided.

5 Claims, 7 Drawing Sheets

OTHER PUBLICATIONS

Choudhuri et al., 1996, "The neurotophins midkine and pleiotrophin are angiogenic and promote tumour growth", Proc. Am. Assoc. for Cancer Research 37:57-58, abstract # 400.

Czubayko et al., 1994, Ribozyme-targeting Elucides a Direct Role of Pleiotrophin in Tumor Growth:, J. Biol. Chem., 269(33):21358-21363.

Dreyfus et al., 1998, "Pleiotrophin: Localizaiton of mRNA and protein in the chicken developing leg", Int'l. J. Dev. Biol., 42(2):189-198 (abstract only).

Fang et al., 1992, "Pleiotrophin stimulates fibroblasts and endothelial and epithelial cells and is expressed in human cancer", J. Biol. Chem. 267(36):25889-25897.

Harris et al., 1994, "Breast cancer angiogenesis-major independent prognostic factor in node negative breast cancer, regulation by multiple angiogenic factors", Proc. Am. Assoc. for Cancer Research 35:185, abstract #1106.

Mitsiadis et al., 1995, "Expression of the heparin-binding cytokines, midkine (MK) and HB-GAM (pleiotrophin) is associated with epithelial-mesenchymal interactions during fetal development and organogenesis", Development, 121(1):37-51 (abstract only).

Obama et al., 1995, "Midkine (MK) expression in extraembryonic tissues, amniotic fluid, and cerebrospinal fluid during mouse embryogenesis", J. Biochem., 118:88-93.

Reigel et al., 1994, "The potential role of the heparin-binding growth factor pleiotrophin in breast cancer", Breast Cancer Res. Treat., 31(2-3):309-314 (abstract only).

Schulte et al., 1996, "Human trophoblast and choriocarcinoma expression of the growth factor pleiotrophin attributable to germ-line Insertion of an endogenous retrovirus", Proc. Natl. Acad. Sci., USA, 93:14759-14764.

Souttou et al., 1998, "Relationship between serum concentrations of the growth factor pleiotrophin and pleiotrophin-positive tumors", J. Nat'l. Cancer Inst., 90(19):1468-1472.

Zhang et al., 1999, "Pleiotrophin and midkine, a family of mitogenic and angiogenic heparin-binding growth and differentiation factors", Current Opinion in Hem., 6(1):44-50.

* cited by examiner

DETECTION OF PLEIOTROPHIN

CROSS REFERENCE TO RELATED APPLICATIONS

This application is the National Phase of International Application PCT/US99/23220 filed Oct. 6, 1999 which designated the U.S. and published under PCT Article 21(2) in English, and which further claims benefit of priority from U.S. Provisional Ser. No. 60/103,197, filed Oct. 6, 1998.

Work described herein was funded, in whole or in part, by the National Institutes of Health Grant # CA108440. The United States Government has certain rights in the invention.

FEDERAL FUNDING

As research performed in this specification was supported by grants from the NIH/NCI (SPORE, CA58185) to A. Wellstein, the government may have rights in the invention.

BACKGROUND OF THE INVENTION

1. Field of the Invention

The present invention relates to novel methods of detecting and measuring levels of the tumor growth factor pleiotrophin (PTN). These measurements can be used to determine the presence of PTN-positive diseases, to determine the relative prognosis of the disease, to determine the efficacy of cytotoxic anticancer drugs, and for molecular targeting of PTN. More particularly, the present invention relates to immunoassays using anti-PTN antibodies to detect and measure levels of PTN in samples. The present invention also relates to kits for detecting and measuring PTN levels.

2. Description of the Related Art

Tumor expansion and metastasis are dependent on growth factors produced by the tumor cells and/or by the stroma (Folkman J, *N. Engl. J. Med.* 333: 1757–1763, 1995) and one would expect in particular that these growth factors, such as angiogenic factors that target sprouting blood vessels, can be shed into the circulation and hence may provide a direct measure of tumor progression. With respect to the significance of growth factor expression and release into the circulation, several clinical studies found elevated levels of basic fibroblast growth factor (bFGF) in the sera of patients with cancer of the prostate (Meyer et al., *Cancer,* 76: 2304–2311, 1995), breast (Sliutz et al., *Anticancer Res.,* 15: 2675–2677, 1995), cervix uteri (Sliutz et al., *Cancer Lett.,* 94: 227–231, 1995) and kidneys (Duensing et al., *Anticancer Res.,* 15: 2331–2333, 1995) as well as in the urine of patients with a wide spectrum of different cancers (Nguygen et al., *J. Natl. Cancer Inst.,* 86: 356–360, 1994). These clinical findings and studies in animals (Soutter et al., *Cancer Research,* 53: 5297–5299, 1993) suggest that in principle angiogenic factors released from tumors can enter the circulation and may serve as useful indicators of tumor progression or as surrogate endpoints of therapeutic efficacy (Wellstein et al., *J. Natl. Cancer Inst.,* 86:328–329).

The tumor growth factor pleiotrophin (PTN) belongs to a family of growth factors that includes midkine (MK) (Kadomatsu et al., *Biochem. Biophys. Res. Commun.,* 3: 1312–1318, 1988). PTN and MK share 50% sequence homology (Laaroubi et al., *Prog. Growth Factor Res.,* 6(1): 25–34, 1995). PTN is involved in growth and differentiation processes that are tightly regulated during development (Schulte et al., *Tumor Angiogenesis,* pp. 273–289, Oxford University Press, 1997), and it is a mitogen for fibroblasts (Fang et al., *J. Biol. Chem.,* 267: 25889–25897, 1992), epithelial cells and endothelial cells (Fang et al., *J. Biol. Chem.,* 267: 25889–25897, 1992 and Delbe et al., *J. Cell Physiol.,* 164: 47–54, 1995). PTN also stimulates plasminogen activator production (Kojima et al., *Biochem. Biophys. Res. Commun.,* 216: 574–581, 1995), induces tube formation of endothelial cells in vitro (Laaroubi et al., *Prog. Growth Factor Res.,* 6(1): 25–34, 1995), and thus can serve as a tumor angiogenesis factor in vivo. Further, PTN is expressed in a variety of tumor cell lines and tumor samples (Fang et al., *J. Biol. Chem.,* 267: 25889–25897, 1992), and pleiotrophin has been found to be oncogenic when overexpressed in NIH3T3 cells (Chauhan et al., *Proc. Natl. Acad. Sci.,* 90: 679–682, 1993) and SW-13 human adrenal carcinoma cells (Fang et al., *J. Biol. Chem.,* 267: 25889–25897, 1992). Furthermore, the growth, angiogenesis and metastasis of PTN-positive melanomas (Czubayko et al., *Biol. Chem.,* 269: 21358–21363, 1994 and Czubayko et al., *Proc. Natl. Acad. Sci.,* 93: 14753–14758, 1996) and the invasion and angiogenesis of choriocarcinoma (Schulte et al., *Proc. Natl. Acad. Sci.,* 93:14759–14764, 1996) was reverted by depleting the tumor cells of their endogenous PTN with specific ribozymes.

Knowing the levels of PTN in samples can play a significant role in diagnosing and prognosticating PTN-positive diseases, monitoring the efficacy of anti-PTN therapeutics, and detecting PTN inhibitors or stimulators. Accordingly, there is a need in the art for methods to detect and measure levels of pleiotrophin in samples and to diagnose pleiotrophin-positive diseases. There is also a need in the art for methods to monitor the effectiveness of therapeutic treatments for pleiotrophin-positive diseases and to test for agents or drugs that inhibit or stimulate pleiotrophin.

OBJECTS AND SUMMARY OF THE INVENTION

It is an object of the invention to provide a method for detecting and measuring the levels of pleiotrophin antigen, particularly PTN in samples.

It is a more specific object of the invention to provide a method utilizing immunoassays for detecting and measuring the levels of pleiotrophin in samples comprising incubating a sample of interest with an antibody directed against pleiotrophin and detecting the antibody-pleiotrophin antigen complex.

It is another specific object of the invention to provide a method for diagnosing pleiotrophin-positive diseases comprising contacting a sample from a patient suspected of having a pleiotrophin-positive disease with antibodies which recognize pleiotrophin, detecting and measuring the presence or absence of antibody-pleiotrophin antigen complexes, and comparing the amount of pleiotrophin to a normal control, wherein an increase in the amount of pleiotrophin over the control indicates the presence of a pleiotrophin-positive disease.

It is yet another specific object of the invention to provide a method for monitoring the effectiveness of therapeutic treatments for a pleiotrophin-positive disease comprising detecting pleiotrophin levels post-treatment and comparing post-treatment pleiotrophin levels to pleiotrophin levels prior to treatment.

It is another specific object of the invention to provide a method for testing agents or drugs which inhibit pleiotrophin comprising administering said agent or drug to cells which express pleiotrophin, detecting pleiotrophin levels, and comparing the pleiotrophin levels to the pleiotrophin levels from cells which did not receive the agent or drug. A decrease in pleiotrophin over the control indicates a pleiotrophin inhibitory agent or drug and an increase in pleiotrophin over the control indicates a pleiotrophin sitmulatory agent or drug.

It is still another object of the invention to provide a method for treating a pleiotrophin-positive disease by administering a therapeutically effective amount of an antibody that binds to pleiotrophin or a fragment thereof.

It is a more specific object of the invention to provide a kit for analyzing samples for the presence of pleiotrophin wherein the kit comprises antibodies directed against pleiotrophin.

It is yet another specific object of the invention to provide a diagnostic or prognostic kit for diagnosing and prognosticating pleiotrophin-positive diseases wherein the kit comprises antibodies directed against pleiotrophin.

BRIEF DESCRIPTION OF THE FIGURES

FIGS. 1A, 1B and 1C illustrate the characterization of the PTN sandwich ELISA assay. The standard curve of 1A displays the sensitivity of the PTN ELISA as ranging from 0.005 to 20 ng/ml. Inset of FIG. 1A: Retention of PTN by the 4B7 monoclonal anti-PTN antibody used as a capturing antibody. 50 ng of PTN were incubated in ELISA wells that had been preadsorbed without (−) or with (+) 4B7 mAb and BSA. Bound PTN was eluted with SDS-PAGE and Western-blotted with a goat anti-PTN antiserum (R&D). 1B shows that the specificity of the ELISA for PTN. PTN 1 ng/ml, MK 10 ng/ml, bFGF 10 ng/ml, or PTN 1 ng/ml plus MK 500 ng/ml were subjected to the ELISA assay. Results are from a representative experiment done in duplicate. 1C shows that serum components other than PTN do not interfere with the detection of PTN by ELISA. PTN concentrations ranging from 0.005 to 20 ng/ml were analyzed in the absence (circles) or presence (triangles) of 50% of normal human serum. Results are from a representative experiment done in duplicate. Standard error bars are shown if they are larger than the symbol size.

DETAILED DESCRIPTION OF THE INVENTION

In accordance with one embodiment of the invention, there is provided a method for detecting and measuring the presence of PTN. The method comprises incubating a sample suspected of containing PTN with anti-PTN antibodies and determining the presence of PTN using techniques such as Western blots, immunoprecipitation, or Enzyme Linked Immunosorbent Assays (ELISAs).

PTN may be determined in a sample from any source. Preferably, PTN is determined in a biological sample. Biological samples include, but are not limited to, blood, serum, urine, cerebrospinal fluid, cell culture supernatants, and tissue.

In a preferred embodiment of the present invention, PTN is detected using a sandwich ELISA that utilizes anti-PTN primary and secondary antibodies. In a more preferred embodiment, a mouse monoclonal antibody (Mab) (4B7) is used as a primary antibody and a biotinylated affinity purified goat anti-PTN polyclonal secondary antibody is used to detect PTN bound to the mouse MAb. The secondary antibody may also be a monoclonal antibody, a mixture of monoclonal antibodies, a mixture of polyclonal antibodies, or a mixture of monoclonal and polyclonal antibodies. These secondary antibodies are preferably coupled to a detectable label, such as radiolabels, flourescent labels and enzymes. The label can be coupled to the secondary antibody by conventional methods known in the art. For example, chemical or physical bonding of the label to the antibody can be used.

Although biotinylated goat anti-PTN polyclonal antibodies are preferred as the secondary antibody, it is also possible to use other polyclonal antibodies produced, for example, in rabbits, mice, and rats. In addition to biotinylated antibodies, one can use antibodies attached to any reporter, such as radiolabeled antibodies or antibodies directly conjugated to alkaline phosphatase (substrates include p-nitrophenyl phosphate (pNPP)), horseradish peroxidase (substrates include 5-aminosalicylic acid (5AS), 2-2' azino-di-(3-ethylbenzthiazoline sulfonate), o-dianisidine, o-phenylenediamine dihydrochloride (OPD), and 3,3'5,5'-tetramethylbenzidne (TMB)), β-galactosidase (substrates include o-nitrophenyl-β-D-galactopyranoside (pNPG) and p-nitrophenyl-β-D-galactopyranoside (pNPG)), or luciferase.

In another embodiment, the present invention can be used to detect and diagnose PTN-positive diseases such as stomach cancer, breast cancer, prostate cancer, pancreatic cancer, and colon cancer. Patients having a PTN-positive disease have elevated levels of PTN when compared to PTN levels in healthy subjects. Measurements of PTN levels, in accordance the with invention, can be used to detect PTN-positive diseases in samples from patients. The method for diagnosing a PTN-positive disease comprises contacting a sample from a patient suspected of having a PTN-positive disease with an antibody that recognize PTN, detecting the presence or absence of a complex formed between sample PTN and the antibody, and comparing the amount of PTN in the sample to PTN levels from normal controls. An increase in the amount of PTN in the sample in comparison to the control is indicative of the presence of a PTN-positive disease. Typical PTN levels in normal healthy subjects range from 0 to 100 pg/ml while abnormal PTN levels range from >100 to 7000 pg/ml.

The present invention is also applicable for detecting and diagnosing any PTN-positive disease including cancer, arthritis, multiple sclerosis, viral infections of the brain, hepatitis, and colitis.

In another embodiment of the invention, the effectiveness of treatment of PTN-positive diseases is monitored by measuring PTN levels in the patient post treatment and comparing the post-treatment PTN levels to initial PTN levels. A decrease in post-PTN levels indicates an effective treatment. PTN levels are measured in accordance with the invention as discussed above. Therapeutic treatments include, but are not limited to, surgical treatment, radiation treatment, chemical treatment, immunotherapy, gene therapy, antisense therapy or a combination thereof.

For example, an anti-PTN antibody can be used to treat PTN-positive diseases. Essentially, a therapeutic amount of the PTN antibody is administered to a patient with a PTN-positive disease. The dose of the anti-PTN antibody to be administered can be determined by methods well known in the art. By binding to PTN protein, the antibody will prevent PTN from functioning as a tumor growth factor, thus, inhibiting tumor growth and angiogenesis. The efficacy of the treatment can be monitored in accordance with the procedure described above and Example I.

Preferred antibodies to treat PTN-positive diseases include, but are not limited to, a monoclonal antibody, a mixture of monoclonal antibodies, polyclonal antibodies, a mixture of polyclonal antibodies, or a mixture of monoclonal and polyclonal antibodies. Additional preferred antibodies include anti-PTN antibodies produced, for example, in rabbits, mice, and rats. More preferably, a human anti-PTN antibody, a humanized anti-antibody, or an anti-PTN antibody produced by any method known in the art can be used.

By "humanized antibody" it is meant an antibody which is less immunogenic in humans. This is achieved by various methods known in the art, for example, one can produce a chimeric humanized antibody by grafting the non-human variable domains which retain antigen binding properties onto a human constant region. Additional methods are disclosed in Morrison et al., *Proc. Natl. Acad. Sci.* 81: 6851–5 (1984); Morrison et al., *Adv. Immunol.* 44: 65–92 (1988); Verhoeyen et al., *Science* 239: 1534–1536 (1988); Padlan, *Molec. Immun.* 28: 489–498 (1991); and Padlan, *Molec. Immun.* 31: 169–217 (1994), all of which are hereby incorporated by reference in their entirety.

The anti-PTN antibodies of the invention may be administered to a human or other animal in an amount sufficient to produce a therapeutic or prophylactic effect. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intraperitoneal, intramuscular, subcutaneous, rectal or vaginal administration. Subcutaneous and intramuscular forms of parenteral administration are generally preferred.

The daily parenteral and oral dosage regimens for employing compounds of the invention will generally be in the range of about 0.05 to 100, but preferably about 0.5 to 10, milligrams per kilogram body weight per day.

The antibodies of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibodies of the invention may also be administered topically. By topical administration is meant non-systemic administration and includes the application of an antibody (or fragment thereof) compound of the invention externally to the epidermis, to the buccal cavity, a instillation of such an antibody into the ear, eye and nose, where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the PTN-positive disease being treated and the animal undergoing treatment, and is ultimately at the discretion of the physician. A suitable topical dose of an antibody of the invention will generally be within the range of about 1 to 100 milligrams per kilogram body weight daily.

In yet another embodiment of the invention, the ability of agents or drugs of interest to inhibit or stimulate pleiotrophin production is determined. Drugs or agents are administered in vitro to cells, for example, neuronal or other brain cells expressing PTN. Following administration of the drug or agent, PTN levels are measured in accordance with the invention. The post-treatment PTN levels are compared to PTN levels of control cells that did not receive the agent or drug. A decrease in PTN in the cell culture medium compared to control cells indicates a PTN inhibitory agent or drug while an increase indicates a PTN stimulatory agent or drug. For example, retinoids are stimulatory agents of PTN.

In yet another embodiment, the present invention can be used to monitor the effectiveness of blocking pleiotrophin production on a molecular level. For example, an agent that destroys pleiotrophin mRNA or blocks the production of pleiotrophin in any manner can be administer to a patient. The levels of pleiotrophin can be measured in accordance with the invention to determine whether the agent and the amount of the agent as well as the time interval for administering the agent were effective or sufficient.

Another embodiment of the invention involves a kit to detect the presence of PTN, such as PTN present in biological samples, to diagnose and prognosticate PTN-positive diseases, and to monitor the effectiveness of therapeutic treatments for PTN-positive diseases. Such a kit comprises an antibody directed against pleiotrophin and ancillary reagents for use in detected the presence of pleiotrophin. Preferably, the kit contains any of: (1) a solid support, such as a microtiter plate, on which to bind a primary anti-PTN antibody; (2) a solution containing the primary antibody; (3) buffer solutions to block unbound sites on the solid support and to wash the solid support; (4) a solution containing the labeled secondary anti body; and (5) PTN protein for a control standard curve.

PTN may be isolated and purified from samples by methods well known in the art such as affinity chromatography, immunoprecipitation, ammonium sulfate precipitation, ethanol precipitation, and anion or cation exchange chromatography. See Sambrook, et al., Molecular Cloning: A Laboratory Manual, $2^{nd}$ edition, Cold Spring Harbor Press, New York, 1989, which is incorporated herein by reference, for additional isolation/purification methods.

In another preferred embodiment, PTN is isolated by immunoassays utilizing anti-PTN antibodies which recognize epitopes of PTN. The antibodies may be polyclonal or monoclonal, preferably monoclonal. In a more preferred embodiment, the anti-PTN antibodies are bound to a solid support. Materials that can be used as solid supports include, but are not limited to, polysaccharide based materials such as cellulose and dextran, silica, nylon, magnetic particles such as beads, and microtiter plates.

In yet another preferred embodiment, the sample of interest is applied to an affinity chromatography column packed with, for example, Protein A or Protein G Sepharose beads (Pharmacia) conjugated to anti-PTN antibodies. After washing the column to remove sufficiently unbound material, the bound PTN antigen is then eluted and, if necessary, quantitated by methods well known in the art.

Another embodiment of the invention includes detecting elevated levels of PTN by adding to a sample a first antibody that binds to PTN. Addition of a second antibody that has an affinity to the first causes the antibody-PTN-antibody complex to precipitate. The precipitated complex can be assayed to determine the amount of PTN present using methods well known in the art.

Having described the preferred embodiments of the present invention, one skilled in the art will recognize that modifications can be made to the preferred embodiments without altering the scope of the invention.

The following examples are provided to further describe the invention, however, the scope of the invention is not limited thereby.

Example I

ELISA Procedure

The mouse monoclonal antibody (4B7) was diluted to 1 µg/ml in Tris-Buffered Saline (TBS; 50 mM Tris HCl pH 7.5, 0.15 M NaCl). 100 µl aliquots of the diluted antibody were incubated in 96 well plates (Corning, N.Y., N.Y.) at 4° C. overnight. The wells were washed three times with TBST (TBS with 0.5% Tween 20). The remaining free binding sites in the wells were then blocked with 200 µl of blocking solution (TBST with 1% BSA) for 2 hours at 4° C. and the wells were washed three times with TBST. Samples suspected of containing PTN were diluted in 2× TBST and 100 µl aliquots of the sample were added to the wells and incubated at room temperature for 1 hour. The wells were then washed three times with TBST and the second antibody (biotinylated, affinity-purified goat anti-human pleiotrophin IgG (R&D Systems, Minneapolis, Minn.)), was added at a concentration of 500 ng/ml and incubated at room temperature for 1 hour. After washing three times with TBST, 100 µl of streptavidin conjugated to alkaline phosphatase at a concentration of 50 ng/ml was added to each well and the plate was incubated for 1 hour at room temperature. The microtiter plate was then washed three times with TBST and incubated with 100 µl p-nitrophenyl phosphate (PNPP) substrate (Pierce) in the dark at 4° C. for 18 hours or at room temperature for 2 hours. Absorbance was measured using a microtiter plate reader at 405 nm.

Figure 1A:
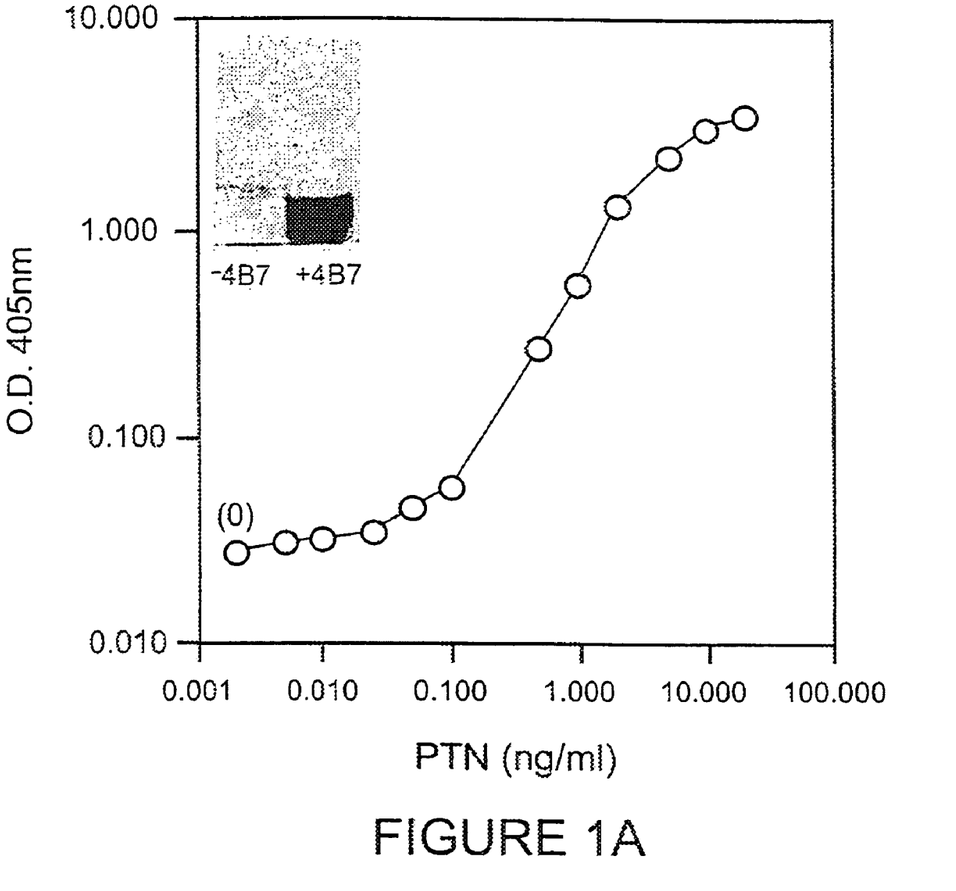

Using the procedure described above, a standard curve for PTN was determined. FIG. 1A shows that the minimum detectable concentration of PTN ranges from 5 to 10 pg/ml. The intra-assay coefficient of variation (CV) was 1.67% and the inter-assay coefficient of variation was 2.10%.

Figure 1B:
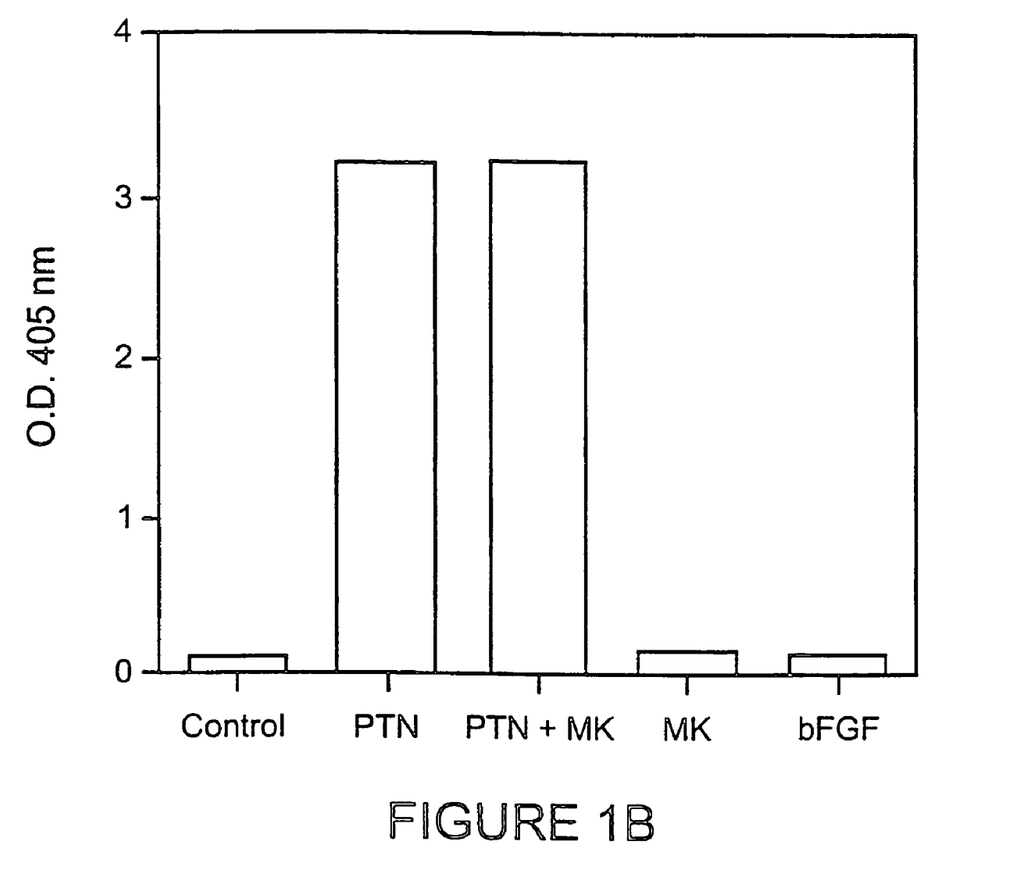

The specificity of the ELISA for PTN was tested against the PTN homologous protein midkine (MK) as well as bFGF, another heparin-binding growth factor. No cross reactivity was observed, and further, co-incubation of PTN with a 500-fold excess of human MK did not alter the signal generated by PTN alone (FIG. 1B). Thus, the PTN ELISA is highly specific for PTN and not MK or bFGF. Since secreted mouse and human PTN protein are identical at the amino acid level (Bohlen et al., *Prog Growth Factor Res.*, 3: 143–157, 1991), the assay cross-reacts with the murine PTN protein.

Figure 1C:
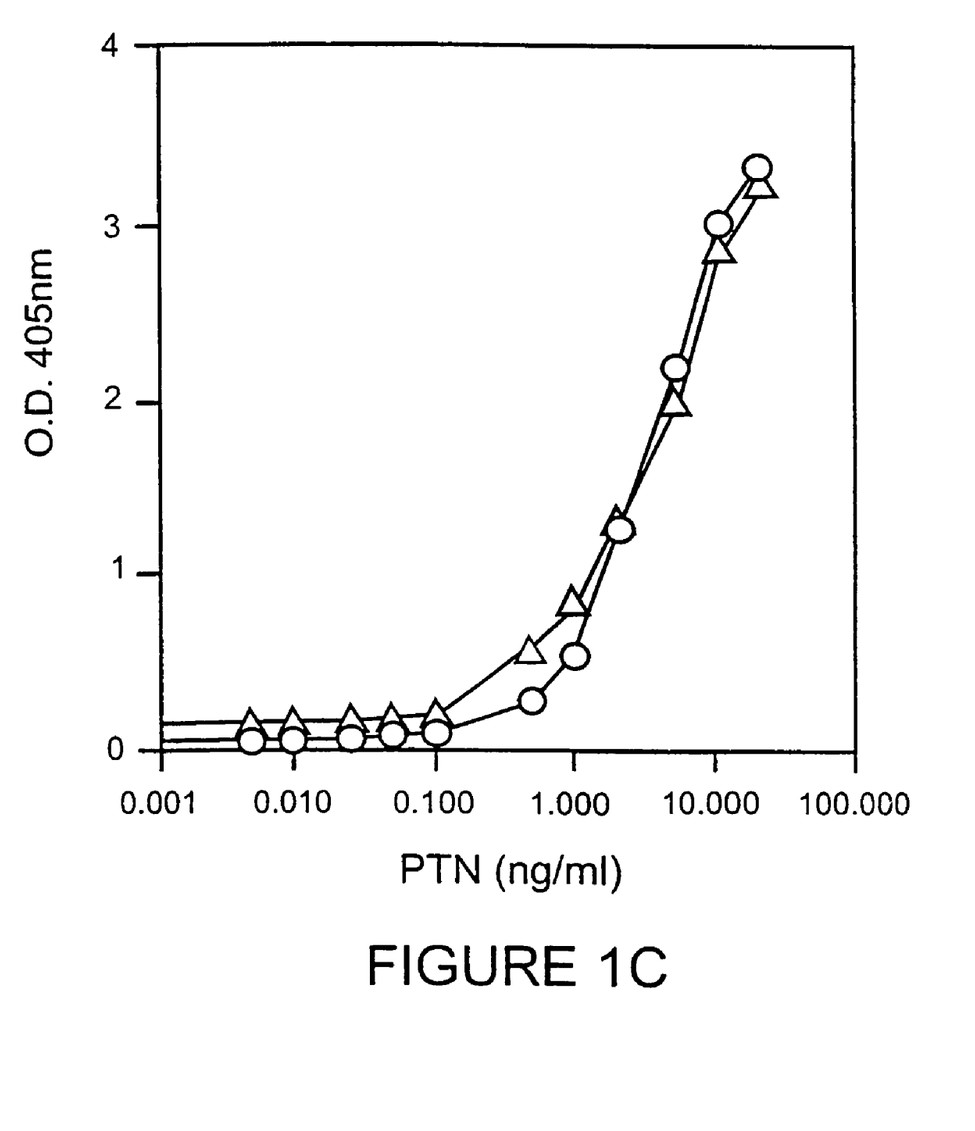

To test whether the ELISA assay could be useful for the detection of PTN in serum samples, the inventors performed experiments in the absence or the presence of human serum. The standard curve of PTN in the presence of serum was similar to that in the absence of serum (FIG. 1C). However, the "background" level in the presence of serum was higher due to low levels of PTN present in normal adult human serum. In the present study, the inventors found mean PTN serum concentrations of 27+6 pg/ml in blood donors (n=28). This quantitation of serum levels confirms an earlier qualitative study in which PTN protein was purified and sequenced from human post-heparin plasma samples (Novotny et al., *Arterioscler Thromb,* 13: 1798–1805, 1993). In contrast to human serum, the serum of athymic nude mice contained PTN levels below the detection limit of the ELISA. Altogether, these results indicate that serum components other than PTN do not interfere with the detection of PTN by the ELISA. Furthermore, the assay is sensitive enough to detect constitutive levels of PTN in normal human serum.

For characterizing the PTN ELISA above, the following reagents were used. Recombinant human PTN produced in SF9 cells using the baculovirus system (Fang et al., *J. Biol. Chem.,* 267: 25889–25897, 1992), recombinant human midkine and affinity-purified goat anti-PTN polyclonal antibodies conjugated and non-conjugated to biotin (R&D Systems, Minneappolis, Minn.), basic fibroblast growth factor (Collaborative Research, Bedford, Mass.), streptavidin-alkaline phosphatase conjugate (Pierce, Rockfork, Ill.), and mouse 4B7 monoclonal anti-PTN antibody (Beau et al., *Exp. Cell. Res.,* 218: 531–539, 1995).

Statistical Analysis.

Analyses were carried out with the PRIZM/GraphPad (San Diego) software. Analysis for normal distribution, Wilcoxon's signed rank, Mann-Whitney and student's t-test as well as Chi-square analysis with Fisher's exact test were used as indicated in the text. All P values are from two-sided tests. Only P-values less than 0.05 were considered statistically significant.

Example II

Detection of PTN in Human Tumor Cell Line Supernatants

Using the procedure outlined in Example I, human tumor cell lines of different origin were screened for the presence of PTN in the culture medium. The PTN ELISA detected 6.3±0.1 and 6.9±0.2 ng of PTN per ml of conditioned medium of subconfluent 1205LU melanoma and MDA-MB 231 breast cancer cells, respectively. Both cell lines had previously been shown to express PTN mRNA and PTN protein. The cell lines were cultivated as reported earlier (Fang et al., *J. Biol. Chem.*, 267: 25889–25897, 1992; Czubayko et al., *Proc. Natl. Acad. Sci.*, 93: 14753–14758, 1996; and Wellstein et al., *J. Biol. Chem.* 267: 2582–2587, 1992). In other human tumor cells found to be PTN-negative by Northern blot analysis (MCF-7, breast cancer; ME-180, squamous cell cancer), the ELISA detected no PTN protein in the supernatants from cells in culture.

Example III

PTN Serum Levels in Mice with Human Xenograft Tumors

Tumor xenografts grown from PTN-positive human tumor cells (MDA-MB 231 breast cancer and 1205LU melanoma) were established and monitored in athymic nude mice as described in Czubayko et al., *Proc. Natl. Acad. Sci.*, 93: 14753–14758, 1996). MCF-7 human breast cancer cells transfected with FGF-4 (MCF-7/FGF-4) served as a negative control because these cells do not produce PTN (Fang et al., *J. Biol. Chem.*, 267: 25889–25897, 1992). Serum samples from mice bearing tumors of at least 1,500 mm$^3$ were analyzed according to Example I.

Figure 2:
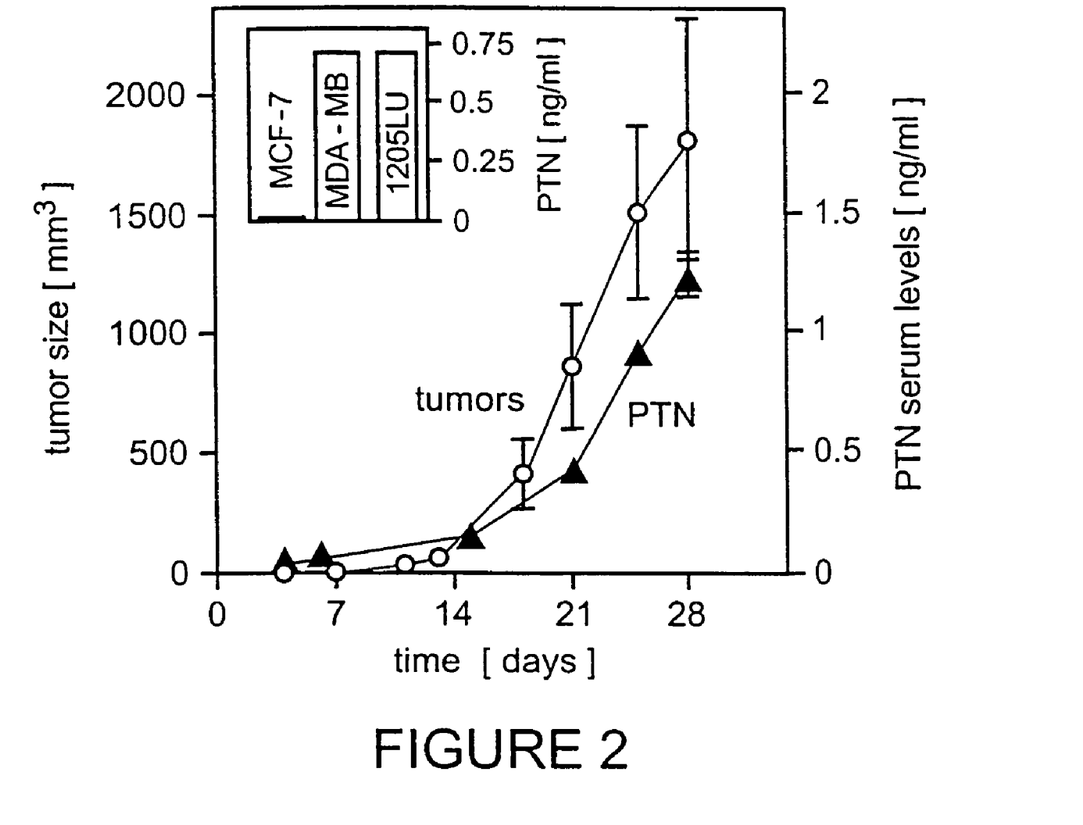
FIG. 2 illustrates xenograft tumor growth and serum levels of PTN in athymic nude mice over time. Subcutaneous tumor growth of 1205LU human melanoma xenografts (open circles) and serum levels of PTN (closed triangles) were determined in the nude mice. Serum was collected from the orbital sinus of subgroups of the mice at different days. Mean±SE values are shown (n=18 tumors; 3 to 6 independent serum samplings at each time point). Inset: Serum levels of PTN in mice with approximately 1,500 mm³ subcutaneous human tumor cell xenografts of different origin. Tumors were grown from PTN-positive human breast cancer cells (MDA-MB 231) and melanoma (1205LU) as well as from PTN-negative, FGF-4-transfected MCF-7 breast cancer cells.

PTN levels in the sera from mice bearing PTN-negative MCR-F/FGF-4 tumors were below the detection limits of the ELISA. In contrast, the sera from mice with the PTN-positive tumor xenografts contained PTN levels greater than 100-fold above the detection limit of the assay (0.7 ng/ml) (FIG. 2, inset).

Processing of Serum Samples

Blood samples collected from mice via the retro-orbital sinus using a Pasteur pipet was allowed to clot overnight at room temperature and centrifuged at 12,000 rpm in a mini-centrifuge at 4° C. to isolate serum. After informed consent, serum samples from patients were drawn pre-operatively and samples from normal subjects (blood donors) were provided by the Blood Bank of the Christain-Albrechts-University (Kiel, Germany). The isolated serum was diluted 1:1 with 2× TBST for use in the ELISA assay in Example I.

Human Subjects

Patients of the Department of Surgery, Christian-Albrechts-University, Kiel (Germany) participated in this study. The age range of patients was: 38 to 90 years for colon, 37 to 78 years for pancreatic and 29 to 86 years for stomach cancer patients. 52%, 46% and 68% of the respective patients were male. Approval by the institutional review board and informed consent of the patients was obtained prior to the study. Serum samples were drawn and stored frozen (−20° C.) for up to four years before processing. Serum samples from randomly selected blood donors served as controls.

Changes in PTN Serum Levels and Tumor Size

To assay whether the levels of PTN detected in the sera reflect the tumor size, the inventors compared serum levels and tumor size of 1205LU melanoma xenografts over a period of several weeks. Increased PTN levels in the serum were detected at the first sign of a palpable tumor nodule (FIG. 2). At this early time point, the tumors had reached <1 mm$^3$ and thus comprised less than 0.01% of the total body mass. Subsequent measured serum levels of PTN increased in parallel with further tumor growth (p<0.01). After surgical removal of the subcutaneous tumors in some of the animals, serum PTN levels decreased.

Example IV

PTN Serum Levels in Cancer Patients Versus Healthy Subjects

Figure 3:
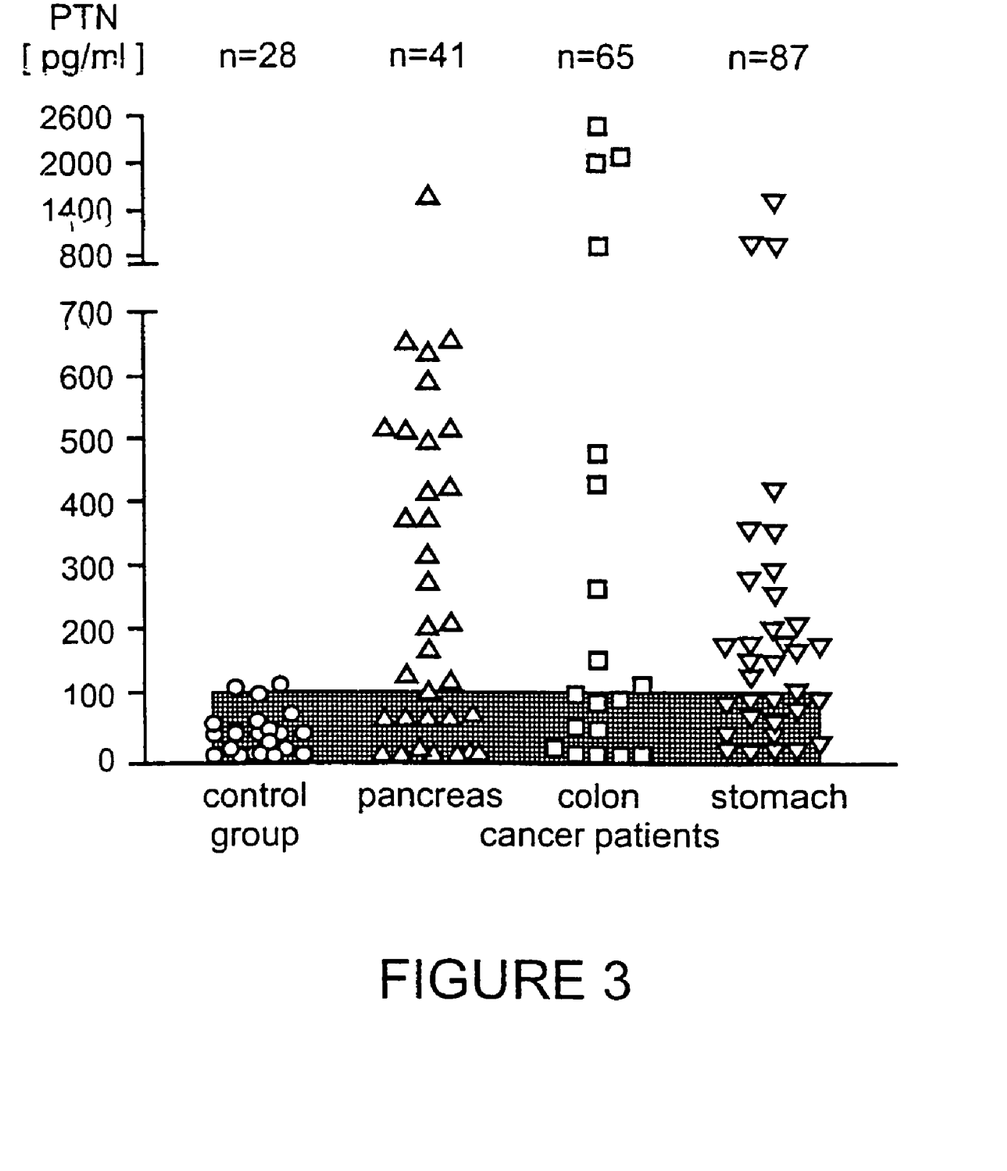
FIG. 3 illustrates the serum levels of PTN in healthy volunteers and patients with different gastrointestinal cancers. 3A shows individual data points, and 3B shows the mean+SE of the different groups.

A non-selected group of healthy blood donors served as a control. In this group, 8 out of 28 subjects showed PTN serum levels below the sensitivity of the ELISA (FIG. 3). The data were normally distributed with the highest level at 107 pg/ml and an average of 27+6 pg/ml (95% C.I.=16 to 41 pg/ml).

PTN serum levels in patients (n=193) with different cancers of the gastrointestinal tract are shown in FIG. 3. 3- to 9-fold elevated values of serum PTN were found in these patients: pancreatic cancer 233±49 pg/ml, n=41 (p<0.0001); colon cancer 142±58 pg/ml, n=65 (p=0.0079); stomach cancer 89±24 pg/ml, n=87, P>0.05). The respective p-values were derived from a Mann-Whitney test.

Figure 5:
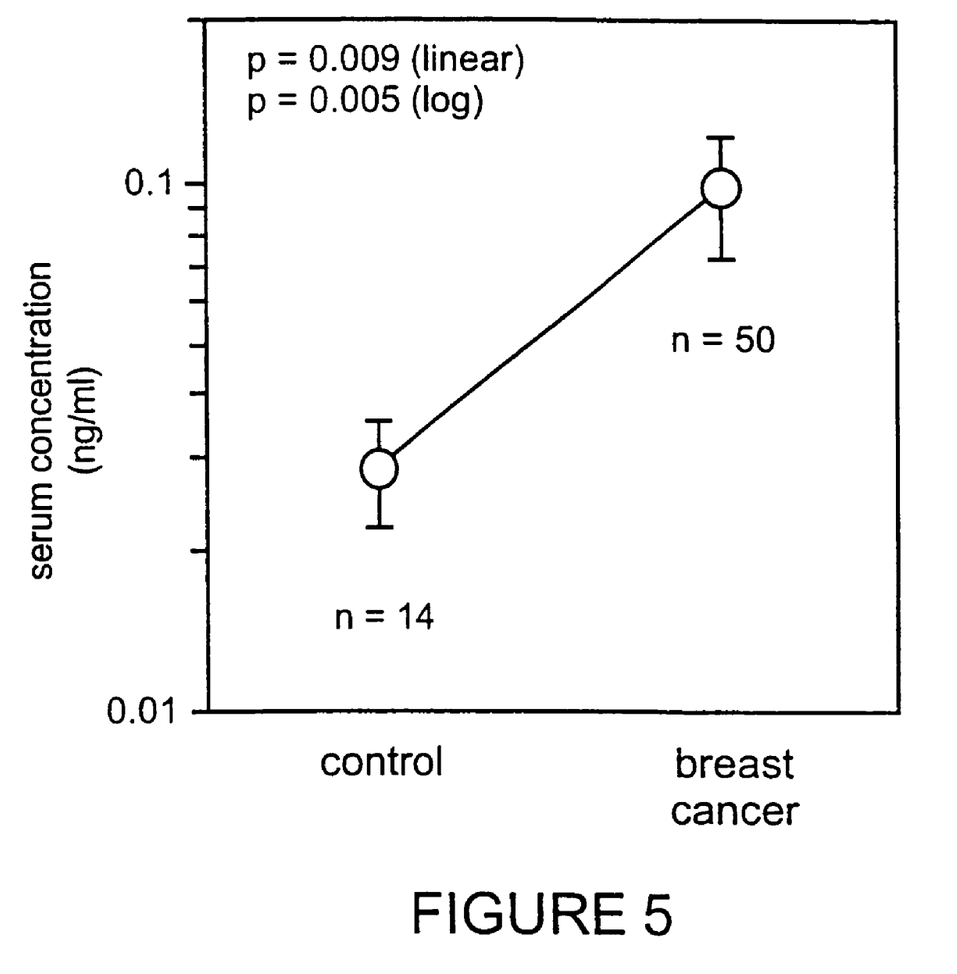
FIG. 5 illustrates a comparison of pleiotrophin levels between healthy subjects and breast cancer patients.

Additionally, FIG. 5 shows the comparison of PTN levels between healthy subjects and breast cancer patients. As in the example above, PTN levels in breast cancer patients are significantly elevated over the healthy control subjects.

Immunohistochemistry of Tumor Samples

Cryostat prepared sections of tumors were acetone-fixed and incubated in a 1:100 dilution of $H_2O_2$ to block endogenous peroxidases. After washing in PBS, the samples were incubated with the primary anti-PTN antibody used in the ELISA (goat anti-human PTN; R&D) diluted to 5 µg/ml (1:20) in 1% BSA in PBS at room temperature for 2 hours or at 4° C. overnight. After washing three times with PBS, the secondary antibody (peroxidase-coupled rabbit anti-goat IgG; Dianova, Hamburg, Germany) was added in 10% ABO human serum and incubated for 1 hour at room temperature. After a further wash in PBS, peroxidase activity was revealed by staining with DAB as a substrate (Vector Lab, Burlingame). The sample was then washed twice in water, dried, and covered.

Figure 4A:
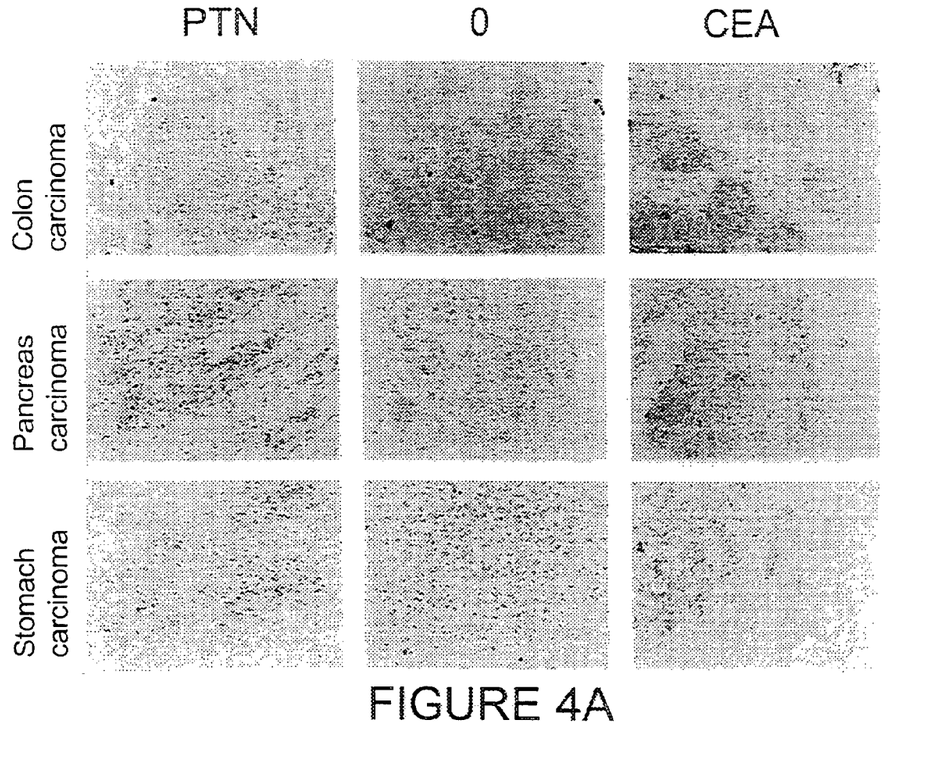
FIG. 4 illustrates the detection of PTN by immunohistochemistry of different gastrointestinal cancers in patients with elevated PTN serum levels (A) or with different serum levels of PTN (B). 4A shows the staining for PTN, a negative control without primary anti-PTN antibody (0), and staining for CEA as a positive control. 4B shows the staining for PTN in samples from patients with colon cancer and different serum levels of PTN as indicated above the respective panel. Note: the staining for PTN in the tumor cells and not the stroma.
Figure 4B:
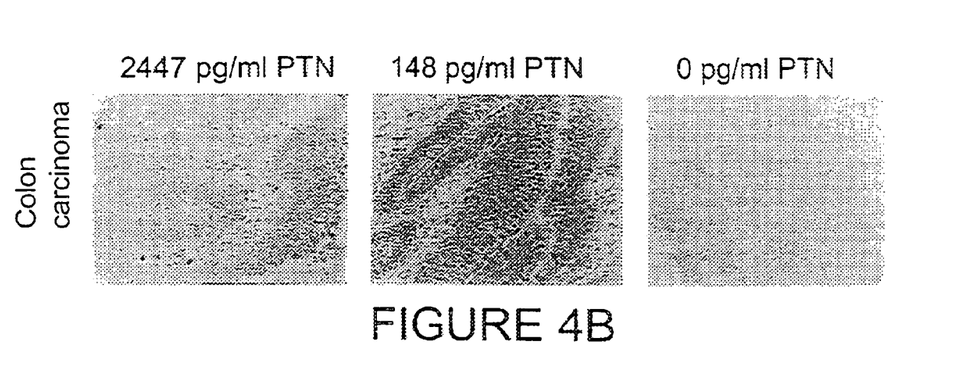

To understand, whether elevated serum levels of PTN indicate gene expression in the patients' tumors, the inventors stained the tumors for PTN by immunohistochemistry and compared the findings with PTN serum levels obtained before surgery. Examples of the staining are shown in FIG. 4 (note that the staining is in the tumor cells) and the correlation between tumor staining and serum levels of PTN are shown in Table I below. The analysis of this data set shows a strong correlation between the presence or absence of PTN in the tumors and elevated or normal serum levels at the time of surgery (p<0.0001). In particular, patients with PTN-negative tumors show no elevated PTN serum levels and elevated serum levels of PTN predict PTN-positivity in tumors.

| | PTN Detection by Immunohistochemistry | | |
|---|---|---|---|
| Tumor | Positive | Negative | p-value |
| Pancreas | 7/9 (77%) | 1/1 (100%) | n.s. |
| Colon | 9/16 (54%) | 4/4 (100%) | <0.05 |
| Stomach | 9/22 (41%) | 12/12 (100%) | <0.01 |
| Total | 25/47 (51%) | 17/17 (100%) | <0.0001 | p-values are based on Fisher's exact test; n.s. = not significant.

Statistical analyses were carried out using the PRIZM/Graphpad (San Diego) software. All P values are from two-sided tests. Only p-values <0.05 were considered statistically significant.

DISCUSSION

The inventors have described a sensitive sandwich ELISA for the growth factor PTN that can detect PTN concentrations in the range of 20 pg/ml to 10 ng/ml and was specific for PTN as it did not recognize the PTN homolog MK or bFGF. Normal human serum did not interfere with the detection of PTN by the ELISA and the assay was sensitive enough to detect constitutive concentrations of PTN in the serum of most of the healthy subjects. In contrast to the findings with human serum samples, PTN levels in the serum from athymic nude mice were below the detection limits of the assay although the assay will cross-react with murine PTN.

The most surprising finding in this study in experimental animals was the fact that even a very low tumor load of less than 0.01% of the body mass led to a significant increase in the serum levels of PTN. Furthermore, it appears the tumor cells themselves and not the tumor stroma are the most likely source of the PTN appearing in serum samples. This conclusion is supported by the lack of an increase in PTN serum levels when PTN-negative tumor cells are grown into xenografts in animals (FIG. 2, inset with MCF-7/FGF-4 tumors).

From the clinical studies, only the groups of patients with pancreatic and colon cancer showed significantly elevated levels of PTN in their serum. Serum levels in patients with stomach cancer were not elevated significantly. The immunohistochemistry data may explain this finding. Only 17% (5 of 30) patients showed no staining for PTN in the pancreas and colon cancer group, whereas twice that portion, 35% (12 of 34) of the stomach cancer samples were negative for PTN. A respectively lower frequency of PTN elevation in the serum is then to be expected in this group. In addition, patients with pancreatic cancer showed the highest portion of PTN serum levels above the range of concentrations seen in healthy subjects (FIG. 3). This may reflect the typically progressed state of this disease and short median survival time of patients with this particular cancer.

In conjunction with the present study in experimental animals, one can speculate that monitoring of PTN serum levels in patients could be a useful measure of residual tumor burden and/or recurrence of tumors after therapy. This is supported by the drop in PTN serum levels after successful tumor removal and the lack thereof with residual tumor mass. Furthermore, in clinical trials with drugs targeting PTN for therapeutic purposes (e.g. synthetic ribozymes), monitoring PTN serum levels is a very attractive way of assessing pharmacologic efficacy of the particular therapeutic molecule or its mode of delivery.

All references cited herein are hereby incorporated by reference in their entirety.

What is claimed is:

1. A method for diagnosis of cancer selected from the group consisting of pancreatic, colon, stomach, melanoma, and breast cancer, comprising the steps of:
   (i) contacting a sample from a patient suspected of having cancer selected from the group consisting of pancreatic, colon, stomach, melanoma, and breast cancer with antibodies which recognize pleiotrophin;
   (ii) detecting the presence or absence of a complex formed between pleiotrophin in the sample and antibodies specific therefor; and
   (iii) comparing the amount of pleiotrophin in said sample to a normal control, wherein an increase in the amount of pleiotrophin in the sample compared to the control indicates the presence of said cancer.

2. A method for evaluating the prognosis of cancer selected from the group consisting of pancreatic, colon, stomach, melanoma, and breast cancer, comprising the following steps:
   (i) contacting a sample from a patient suspected of having cancer selected from the group consisting of pancreatic, colon, stomach, melanoma, and breast cancer with antibodies which recognize pleiotrophin;
   (ii) detecting the presence or absence of a complex formed between pleiotrophin in the same and antibodies specific therefor; and
   (iii) comparing the amount of pleiotrophin in said sample to a normal control, wherein an increase in the amount of pleiotrophin in the sample compared to the control indicates the prognosis of said cancer.

3. A method for monitoring the effectiveness of a therapeutic treatment of cancer selected from the group consisting of pancreatic, colon, stomach, melanoma, and breast cancer, comprising the following steps:
   (i) contacting a sample from a patient who has undergone therapeutic treatment of cancer selected from the group consisting of pancreatic, colon, stomach, melanoma, and breast cancer with antibodies which recognized pleiotrophin;
   (ii) detecting the level of complexes formed between pleiotrophin and antibodies specific therefor; and
   (iii) comparing an amount of post-treatment pleiotrophin levels to an initial pleiotrophin levels prior to treatment, wherein a decrease in post-pleiotrophin levels indicates an effective treatment.

4. The method according to claim 3, wherein said treatment is selected from the group consisting of surgical treatment, radiation treatment, and chemical treatment.

5. An in vitro method for testing agents or drugs that inhibit or increase pleiotrophin, said method comprising:
   (i) administering a drug or agent to cells that express pleiotrophin;
   (ii) detecting pleiotrophin using a mouse monoclonal antibody directed against pleiotrophin;
   (iii) comparing the amount of pleiotrophin to control cells that did not receive said drug or agent, wherein a decrease in pleiotrophin compared to control indicates a pleiotrophin inhibitory agent or drug and an increase in pleiotrophin compared to control indicates a pleiotrophin stimulatory agent or drug.

* * * * *